US006595973B2

(12) United States Patent
Sugito (10) Patent No.: US 6,595,973 B2
(45) Date of Patent: Jul. 22, 2003

(54) PULL-ON DISPOSABLE WEARING ARTICLE

(75) Inventor: Tomoko Sugito, Kagawa-ken (JP)

(73) Assignee: Uni-Charm Corp., Ehime-ken (JP)

(*) Notice: Subject to any disclaimer, the term of this patent is extended or adjusted under 35 U.S.C. 154(b) by 0 days.

(21) Appl. No.: 09/842,448

(22) Filed: Apr. 26, 2001

(65) Prior Publication Data

US 2001/0037102 A1 Nov. 1, 2001

(30) Foreign Application Priority Data

Apr. 27, 2000 (JP) ........................................ 2000-128217

(51) Int. Cl.[7] .............................................. A61F 13/15
(52) U.S. Cl. .................................................. 604/385.13
(58) Field of Search ...................... 604/385.01, 385.19, 604/385.13, 385.02, 385.04, 385.06

(56) References Cited

U.S. PATENT DOCUMENTS

| | | | | |
|---|---|---|---|---|
| 3,024,788 A | * | 3/1962 | Lane ........................... | 128/285 |
| 3,369,545 A | * | 2/1968 | Wanberg ..................... | 128/287 |
| 3,604,423 A | * | 9/1971 | Fraser ......................... | 128/290 |
| 3,865,110 A | * | 2/1975 | Traverse ..................... | 128/284 |
| 3,890,973 A | * | 6/1975 | Davis et al. ................ | 128/286 |
| 3,920,019 A | * | 11/1975 | Schaar ........................ | 128/287 |
| 3,927,674 A | * | 12/1975 | Schaar ........................ | 128/287 |
| 4,085,753 A | * | 4/1978 | Gellert ........................ | 128/284 |
| 4,430,087 A | * | 2/1984 | Azpiri ......................... | 604/385 |
| 4,493,713 A | * | 1/1985 | Izzo ............................ | 604/385 |
| 4,604,096 A | * | 8/1986 | Dean et al. ................. | 604/385 |
| 4,923,455 A | * | 5/1990 | Dean et al. ............... | 604/385.1 |
| 4,931,052 A | * | 6/1990 | Feldman ................... | 604/385.1 |
| 4,968,311 A | * | 11/1990 | Chickering et al. ...... | 604/385.1 |
| 4,968,312 A | * | 11/1990 | Khan ......................... | 604/388 |
| 5,037,414 A | * | 8/1991 | Booth ...................... | 604/385.1 |
| 5,071,414 A | * | 12/1991 | Elliott ...................... | 604/385.1 |
| 5,093,935 A | | 3/1992 | Countee, Jr. | |
| 5,141,505 A | * | 8/1992 | Barrett ..................... | 604/385.1 |
| 5,241,710 A | | 9/1993 | Lockhart | |
| 5,304,158 A | * | 4/1994 | Webb ....................... | 604/385.1 |
| 6,475,204 B1 | * | 11/2002 | Walker ................... | 604/385.06 |

FOREIGN PATENT DOCUMENTS

| | | |
|---|---|---|
| EP | 0 496 716 A1 | 7/1992 |
| EP | 0 684 029 A2 | 11/1995 |
| EP | 0 875 226 A2 | 11/1998 |
| FR | 2 675 993 | 11/1992 |
| JP | 7-265355 | 10/1995 |
| JP | 10-295725 | 10/1998 |

OTHER PUBLICATIONS

Copy of European Search Report dated Aug. 2, 2001.

* cited by examiner

*Primary Examiner*—Weilun Lo
*Assistant Examiner*—Jacqueline F Stephens
(74) *Attorney, Agent, or Firm*—Butzel Long

(57) ABSTRACT

Here is disclosed a pull-on disposable wearing article formed by connecting front and rear waist regions to each other wherein an auxiliary sheet having a given area and placed upon outer surface of a backsheet extends from a crotch region into the front waist region and comprises a free end zone lying in the front waist region and circumferentially extending and fixed side edge zones longitudinally extending along the transversely opposite side edges in the front waist region as well as in the crotch region and fixed to the outer surface of the backsheet.

6 Claims, 7 Drawing Sheets

PULL-ON DISPOSABLE WEARING ARTICLE

BACKGROUND OF THE INVENTION

This invention relates to a pull-on disposable wearable article and more particularly to such wearable article such as a pull-on disposable diaper, training pants or incontinent pants.

Japanese Patent Application Publication No. 1998-295725A describes a pull-on disposable wearable article basically comprising a liquid-pervious topsheet, a liquid-impervious backsheet and a liquid-absorbent core disposed between these two sheets wherein front and rear waist regions are connected to each other along transversely opposite side edges thereof to form a waist-hole and a pair of leg-holes and wherein an auxiliary flap is attached to outer surface of the backsheet in the front and/or rear waist regions. In the article disclosed in the Publication, the auxiliary flap has its transversely opposite side edges fixed to the corresponding side edges of the front waist region and its upper end fixed to peripheral edge of the waist-hole in the front waist region so as to form a pocket opening downwardly of the article.

For disposal of the article, the article is longitudinally rolled up from the crotch region toward the waist-hole with the rear waist region inside, then the auxiliary flap is folded back toward the rear waist region to turn the pocket inside out and the rolled up article is tucked away in the pocket turned inside out.

The article disclosed in the Publication can put the waist-hole as well as the leg-holes into the pocket merely by rolling the article up. However, it is apprehended that excretion having been discharged within the article might be squeezed out through the waist-hole and/or the leg-holes as the article is rolled up.

SUMMARY OF THE INVENTION

It is an object of this invention to provide a disposable wearing article of pants-type enabling a waist-hole as well as leg-holes to be kept closed for disposal of the used article so that leakage of excretion through these holes can be reliably avoided without a necessity for rolling it up.

According to this invention, there is provided a pull-on disposable wearable article comprising a liquid-pervious topsheet, a liquid-impervious backsheet and a liquid-absorbent core disposed between these two sheets so as to configure first and second waist regions opposed to each other and a crotch region extending between these two waist regions wherein the first and second waist regions are connected to each other along transversely opposite side edges thereof to form a waist-hole and a pair of leg-holes.

According to the present invention, an auxiliary sheet having a given area and placed upon an outer surface of the backsheet extends from the crotch region into the first and/or second waist regions and comprises a free end zone lying in the first waist region and extending in circumferential direction and fixed side edge zones longitudinally extending along the transversely opposite side edges in the first and second waist regions and the crotch region and fixed to the outer surface of the backsheet.

According to one embodiment of this invention, the auxiliary sheet is fixed to the outer surface of the backsheet along a sealed zone extending parallel to the free end zone across a substantially middle zone of the crotch region and wherein the backsheet cooperates with the auxiliary sheet to form a pocket opening toward the waist-hole.

According to another embodiment of this invention, a fastening zone adapted to fasten the auxiliary sheet to the outer surface of the backsheet extends in the circumferential direction along the free end zone of the auxiliary sheet.

According to still another embodiment of this invention, an elastically stretchable member extending in the circumferential direction is attached under tension to the free end zone.

According to further another embodiment of this invention, the auxiliary sheet is elastically stretchable in the circumferential direction and bonded under tension in the circumferential direction to the outer surface of the backsheet.

DETAILED DESCRIPTION OF THE PREFERRED EMBODIMENTS

Details of the disposable wearing article of pants-type according to this invention will be more fully understood from the description of disposable diaper as one embodiment given hereunder with reference to the accompanying drawings.

Figure 1:
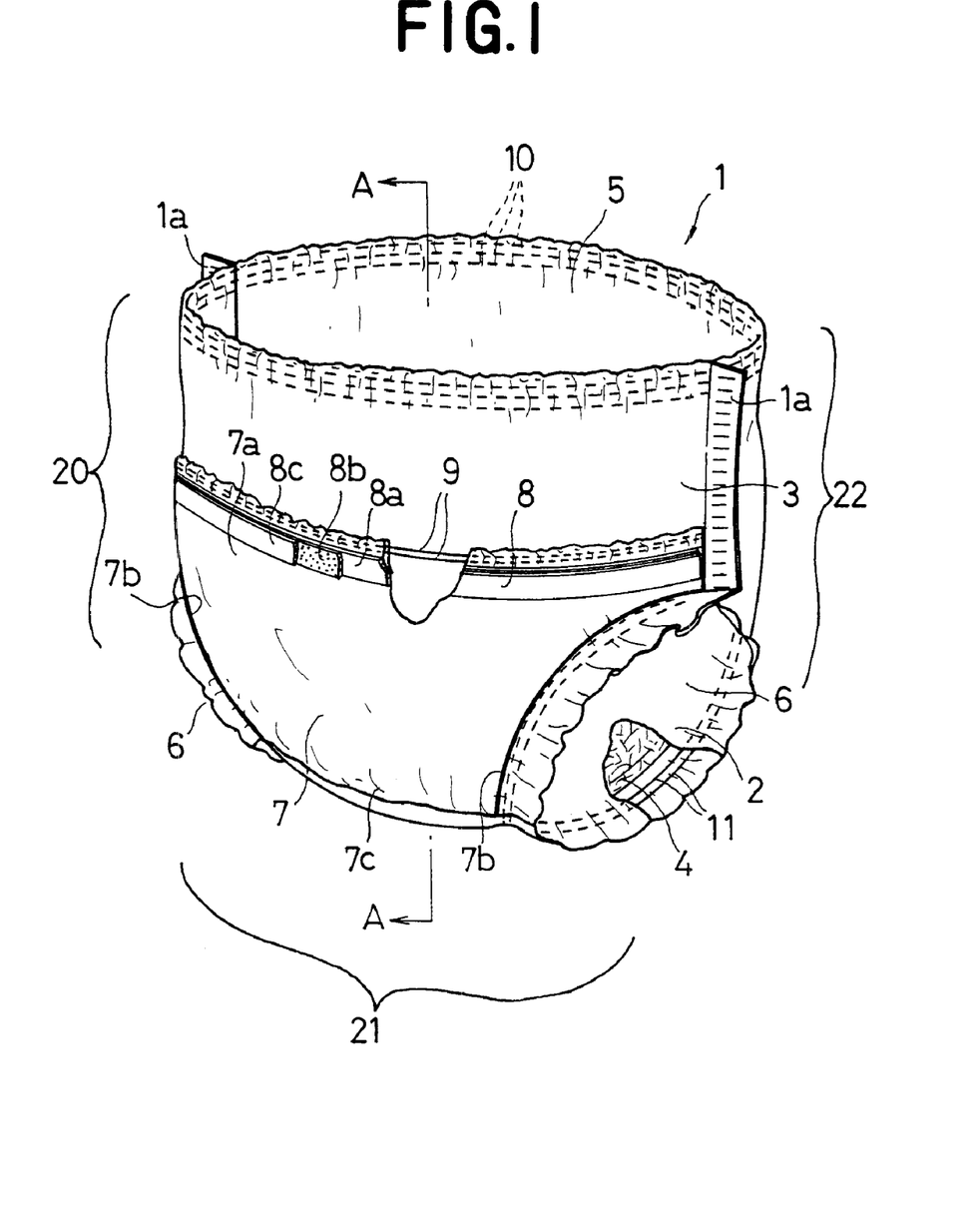
FIG. 1 is a perspective view showing a disposable diaper as viewed from the side of a front waist region and partially broken away.
Figure 2:
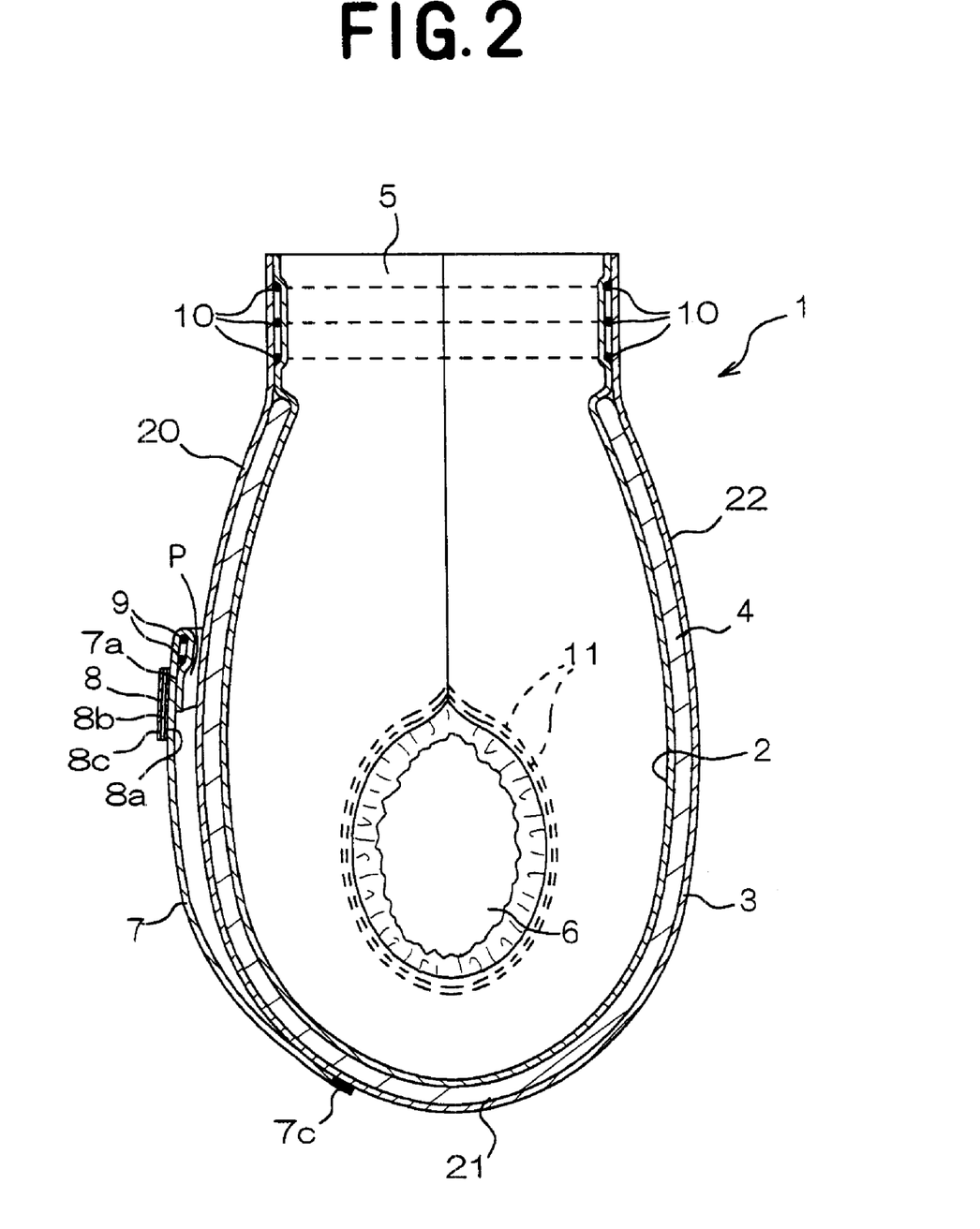
FIG. 2 is a sectional view taken along line A—A in FIG. 1.

FIG. 1 is a perspective view showing a disposable diaper 1 as viewed from the side of a front waist region 20 and partially broken away and FIG. 2 is a sectional view taken along a line A—A in FIG. 1. The diaper 1 comprises a liquid-pervious topsheet 2, a liquid-impervious backsheet 3 and a liquid-absorbent core 4 disposed between the top- and backsheets 2, 3. The liquid-absorbent core 4 is entirely covered with and bonded to liquid-pervious tissue paper (not shown) with interposition of which the core 4 is bonded to inner surface of the topsheet 2 and/or the backsheet 3.

The diaper 1 is longitudinally composed of the front waist region 20, a rear waist region 22 and a crotch zone 21 extending between the front and rear waist regions 20, 22. The front and rear waist regions 20, 22 are put flat together and bonded together along respective transversely opposite side edges 1a extending longitudinally of the diaper 1 so as to define a waist-hole 5 opening upward as viewed in FIG. 1 and a pair of leg-holes 6 opening laterally also as viewed in FIG. 1.

Along peripheral edge of the waist-hole 5, a plurality of elastically stretchable members 10 are disposed between the top- and backsheets 2, 3 and bonded under tension to inner surface of the topsheet 2 and/or the backsheet 3. Similarly, along peripheral edges of the respective leg-holes 6, a plurality of elastically stretchable members 11 are disposed between the top- and backsheets 2, 3 and bonded under tension to inner surface of the topsheet 2 and/or the backsheet 3. The presence of the elastic members 10, 11 respectively enables the peripheral edges of the waist- and leg-holes 5, 6 to have circumferential elastic stretchability. Referring to FIG. 1, the respective elastic members 10, 11 have been relieved of tension and consequently gathers are formed along the peripheral edges of the waist- and leg-holes 5, 6.

The diaper 1 is provided on outer surface of the backsheet 3 with an auxiliary sheet 7 adapted to hold the used diaper 1 in its folded state for disposal. This auxiliary sheet 7 has a given area and extends from the crotch region 21 into the front waist region 20. More specifically, the auxiliary sheet 7 is defined by a free end zone 7a lying at a substantially middle level of the front waist region 20 and circumferentially extending between the transversely opposite side edges 1a in the front waist region 20, transversely opposite fixed side edge zones 7b longitudinally extending along the transversely opposite side edges lain the front waist region 20 and the crotch region 21, and a fixed end zone 7c (sealed zone) extending parallel to the free end zone 7a across a substantially middle zone of the crotch region 21. While the auxiliary sheet 7 is illustrated to extend from the crotch region 21 into the front waist region 20, an alternative arrangement is also possible in which the auxiliary sheet 7 extends from the crotch region 21 into the rear waist region 22.

An elastically stretchable member 9 extending circumferentially is attached under tension to the free end zone 7a of the auxiliary sheet 7 so as to be covered with a part of the free end zone 7a. The auxiliary sheet 7 has its fixed side edge zones 7b and fixed end zone 7c bonded to the outer surface of the backsheet 3 so that the auxiliary sheet 7 cooperates with the backsheet 3 to form a pocket P opening toward the waist-hole 5. The auxiliary sheet 7 is provided on its outer surface with a fastening zone 8 circumferentially extending along the free end zone 7a so that the auxiliary sheet 7 may be fastened to the outer surface of the backsheet 3 in this fastening zone 8.

The fastening zone 8 comprises a flexible plastic sheet 8a, pressure-sensitive adhesive 8b applied on outer surface of the plastic sheet 8a and a peelable protective sheet 8c covering the pressure-sensitive adhesive 8b. The plastic sheet 8a has its inner surface fixed to the outer surface of the auxiliary sheet 7 immediately below the elastic member 9. Alternatively, it is possible to form the fastening zone 8 on the inner surface of the auxiliary sheet 7 so that the fastening zone 8 circumferentially may extend along the free end zone 7a.

Figure 3A:
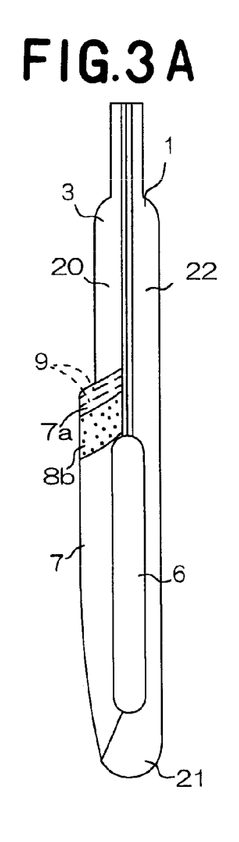
FIG. 3 is a diagram schematically illustrating steps of tucking away the diaper of FIG. 1 in the pocket P.
Figure 3B:
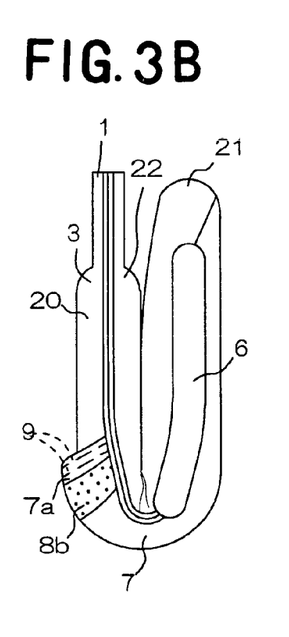
Figure 3C:
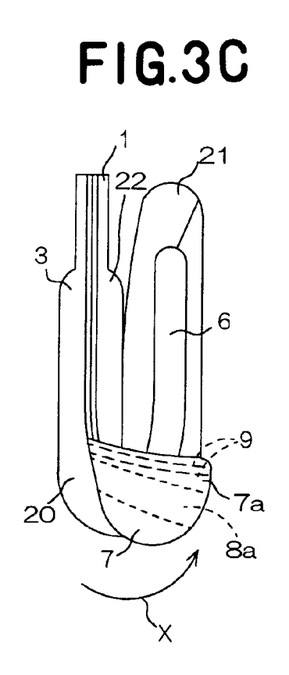
Figure 3D:
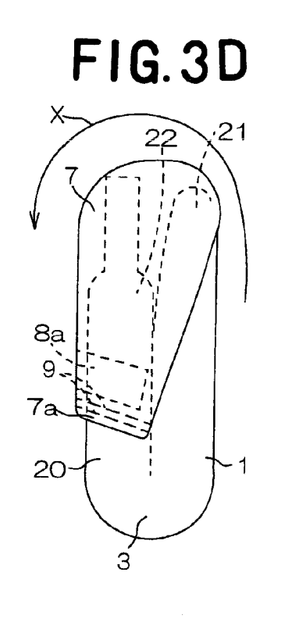
Figure 4:
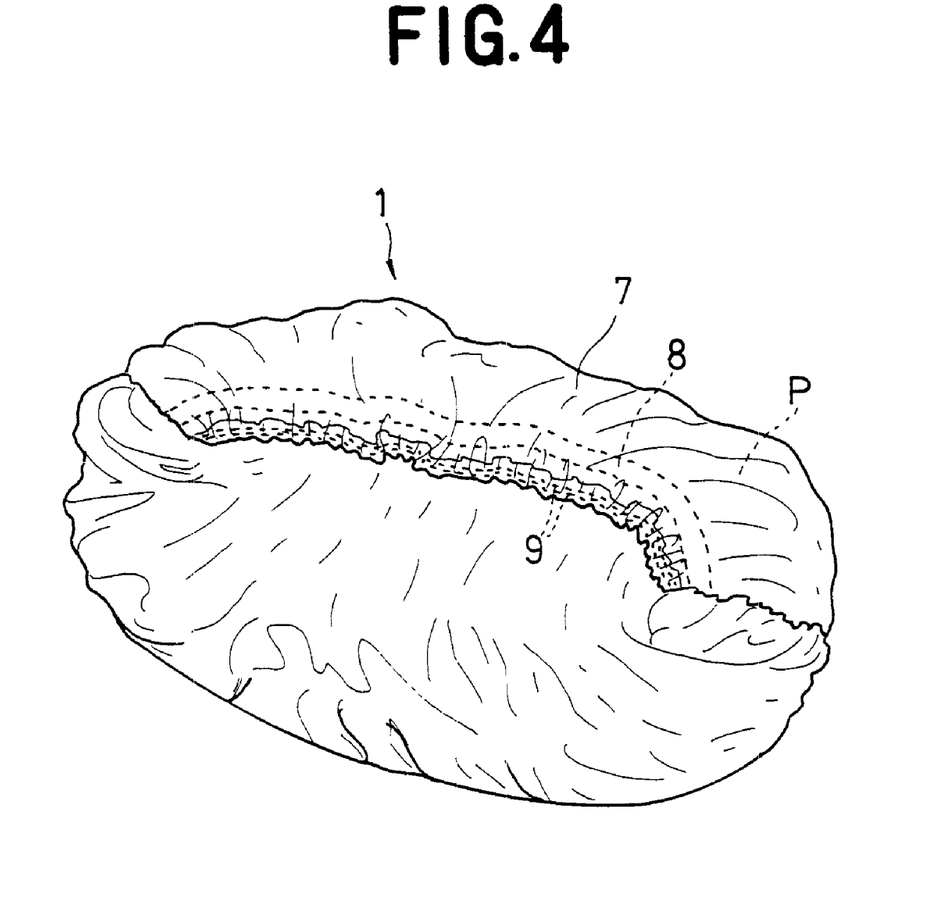
FIG. 4 is a perspective view showing the used diaper tucked away in the pocket P for disposal.

FIGS. 3A–3D are diagrams schematically illustrating steps of tucking away the used diaper 1 in the pocket P and FIG. 4 is a perspective view showing the diaper 1 tucked away in the pocket P for disposal. From the state of FIG. 3A, the diaper 1 is folded in two with the rear waist region 22 inside, i.e., with the rear waist region 22 placed upon the crotch region 21. It should be understood that the protective sheet 8c has been peeled off from the fastening zone 8 to expose the pressure-sensitive adhesive 8b before the diaper 1 is folded in two.

After the diaper 1 has been folded in two as illustrated in FIG. 3B, the free end zone 7a of the auxiliary sheet 7 is pulled in a direction indicated by an arrow X toward the crotch region 21 as illustrated in FIGS. 3C and 3D, then the auxiliary sheet 7 is folded back toward the front waist region 20 to turn the pocket P inside out. The diaper 1 is tucked away within the pocket P turned inside out. Then the auxiliary sheet 7 is fastened in the vicinity of its free end zone 7a to the outer surface of the front waist region 20 by means of the pressure-sensitive adhesive 8b.

Of the diaper 1 tucked away in the pocket P, the waist-hole 5 as well as the leg-holes 6 are completely received in this pocket P as illustrated by FIG. 4 and the opening of the pocket P is sealed by means of the pressure-sensitive adhesive 8b. After disposal of the diaper 1, it is not apprehended that the waist-hole 5 as well as the leg-holes 6 might be exposed from the pocket P. It is also not apprehended that undesirable odor and/or excretion might leak through the waist-hole 5 as well as the leg-holes 6 might be exposed from the pocket P.

It is unnecessary for the diaper 1 according to this invention to be rolled up for disposal thereof after used. Instead, the used diaper 1 folded in two may be tucked away in the pocket P to confine the waist- and leg-holes 5, 6. In this way, an anxiety that excretion having been discharged in the diaper 1 might be forced out through the waist- and leg-holes 5, 6 as the used diaper 1 is rolled up for disposal can be reliably eliminated. Additionally, tacking the used diaper 1 away in the pocket P can be achieved merely by folding it in two and the conventional troublesome operation of rolling up it can be eliminated. Obviously, it is also possible to tuck the used diaper 1 in the pocket P by longitudinally rolling the used diaper 1 from the crotch region 21 up toward the rear waist region 22 or by folding the used diaper 1 in two or more.

With the arrangement in which the elastic member 9 is attached under tension to the free end zone 7a of the auxiliary sheet 7, it will be unnecessary to form the fastening zone 8 on the outer surface of the auxiliary sheet 7. In this case, the free end zone 7a of the auxiliary sheet 7 circumferentially contracts and the opening of the pocket P is correspondingly reduced as the used diaper 1 is tucked away in the pocket P. As a result, there is no apprehension that the waist-hole 5 as well as the leg-holes 6 might be exposed from the opening of the pocket P.

Figure 5:
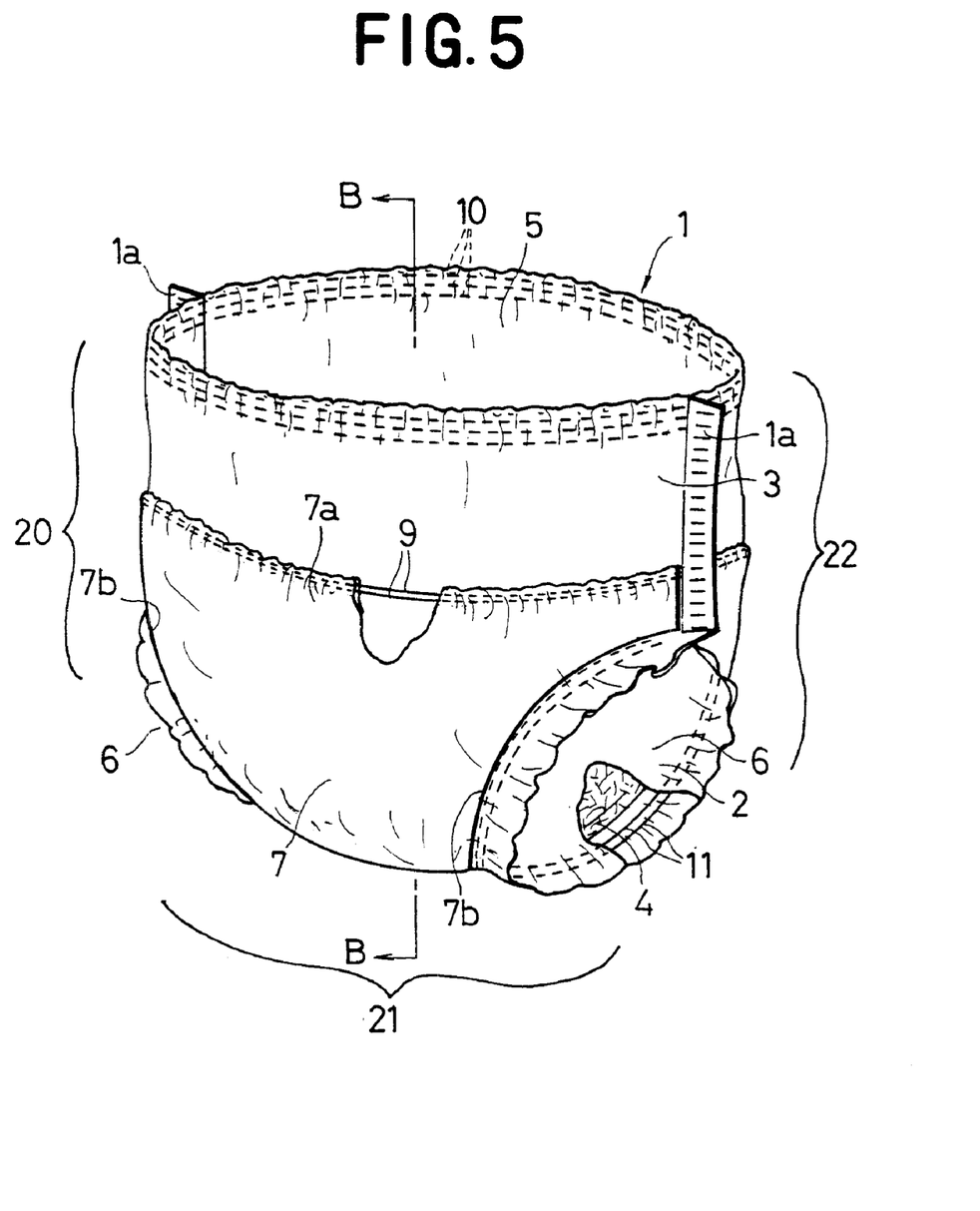
FIG. 5 is a perspective view showing another embodiment of the diaper 1 as viewed from the side of the front waist region and partially broken away.
Figure 6:
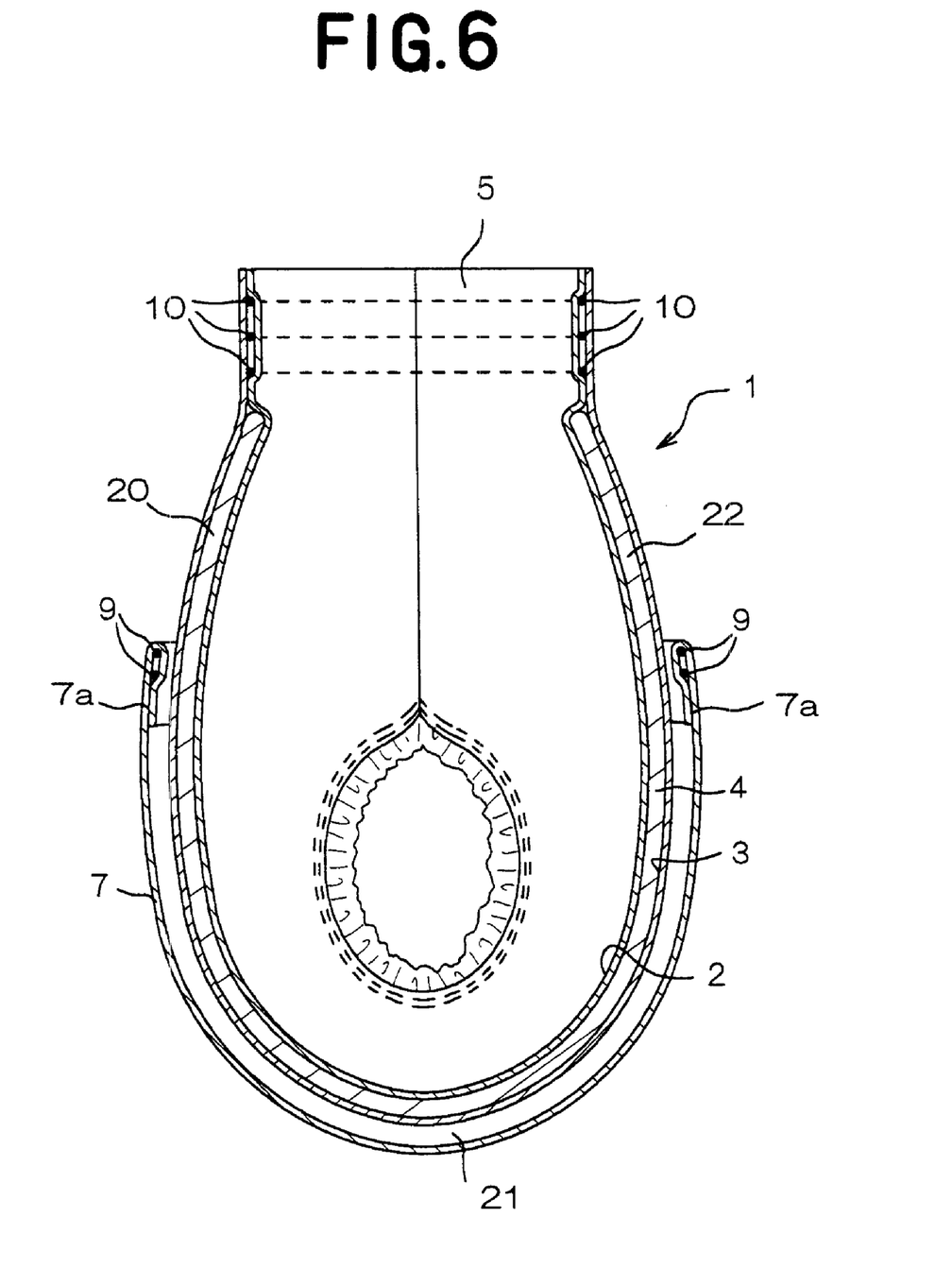
FIG. 6 is a sectional view taken along line B—B in FIG. 5.

FIG. 5 is a perspective view showing another embodiment of the diaper 1 as viewed from the side of the front waist region 20 and partially broken away and FIG. 6 is a sectional view taken along line B—B in FIG. 5. This embodiment is similar to that shown by FIG. 1 in that the diaper 1 basically comprises a liquid-pervious topsheet 2, a liquid-impervious backsheet 3 and a liquid-absorbent core 4 disposed between the top- and backsheets 2, 3 and entirely covered with and bonded to liquid-pervious tissue paper (not shown) wherein the front and rear waist regions 20, 22 are put flat together and bonded together along respective transversely opposite side edges 1a so as to define a waist-hole 5 and a pair of leg-holes 6.

In the front and rear waist regions 20, 22, a plurality of elastically stretchable members 10 are attached under tension to respective peripheral edges of the waist-hole 5 and a plurality of elastic stretchable members 11 are attached under tension to respective peripheral edges of the leg-holes 6.

The diaper 1 is provided on outer surface of the backsheet 3 with an auxiliary sheet 7 adapted to hold the used diaper 1 in its folded state for disposal. This auxiliary sheet 7 has a given area and extends from the crotch region 21 into the front and rear waist regions 20, 22. More specifically, the auxiliary sheet 7 lies in the front waist region 20 as well as in the rear waist region 22 and is defined by a pair of free end zones 7a circumferentially extending between respective transversely opposite side edges of the front and rear waist regions 20, 22, and fixed side edge zones 7b longitudinally along respective transversely opposite side edges 1a of the front and rear waist regions 20, 22 as well as the crotch region 21.

Elastically stretchable members 9 extending circumferentially are attached under tension to the respective free end zones 7a of the auxiliary sheet 7 so as to be covered with respective part of the free end zones 7a. The auxiliary sheet 7 has its fixed side edge zones 7b bonded to the outer surface of the backsheet 3.

Figure 7A:
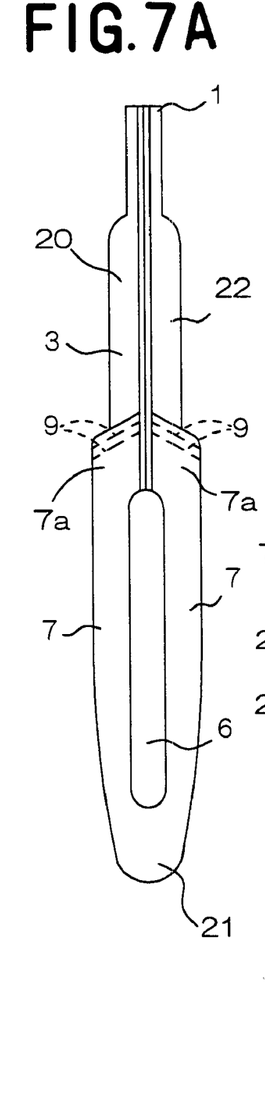
FIG. 7 is a diagram schematically illustrating steps of putting the auxiliary sheet over the diaper of FIG. 5.
Figures 7B, 7C:
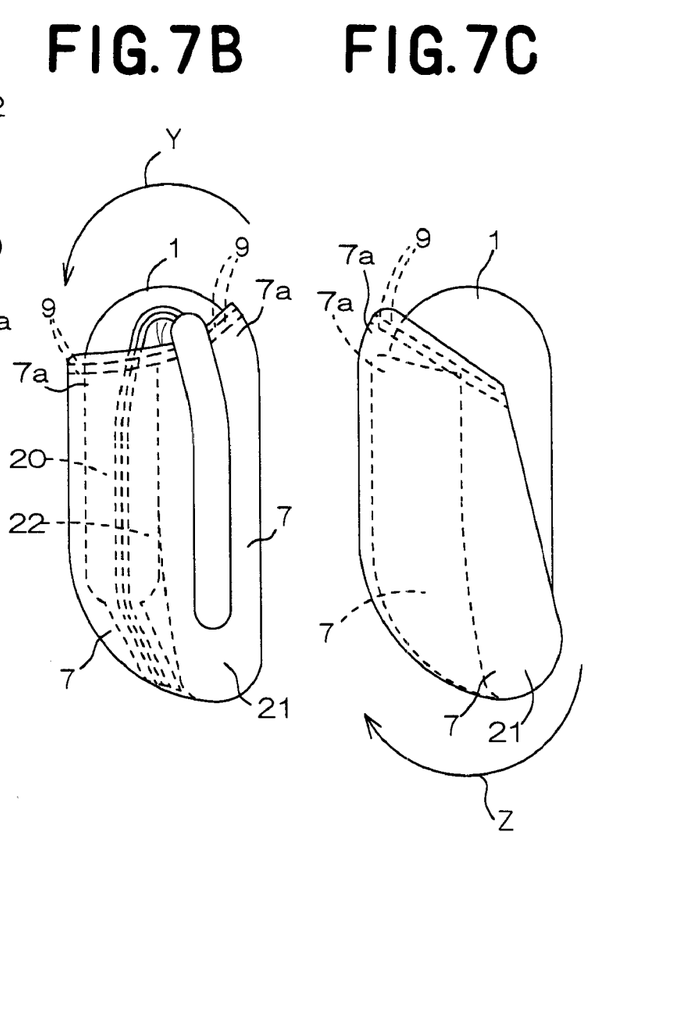

FIGS. 7A–7C are diagrams schematically illustrating steps of putting the auxiliary sheet 7 over the used diaper 1 of FIG. 5. From the state of FIG. 7A, the diaper 1 is folded in two with the front waist region 20 inside, i.e., with the front waist region 20 placed upon the crotch region 21. Then, the peripheral edge of the waist-hole 5 is inserted from the free end zone 7a of the auxiliary sheet 7 lying in the front waist region 20 into a space defined between the auxiliary sheet 7 and the backsheet 3 as indicated by an arrow Y in FIG. 7B.

After the diaper 1 has been folded in two as illustrated in FIG. 7B, the free end zone 7a of the auxiliary sheet 7 lying in the rear waist region 22 is pulled in a direction indicated by an arrow Z in FIG. 7C toward the crotch region 21, then the auxiliary sheet 7 is folded back toward the front waist region 20 to turn the auxiliary sheet 7 inside out. Thus the diaper 1 is tucked away in a space defined between the auxiliary sheet 7 and the backsheet 3.

Once the used diaper 1 has been tucked away in the space defined between the auxiliary sheet 7 and the backsheet 3, there is no anxiety that the waist- and leg-holes 5, 6 might be exposed from this space. After disposal, it is not apprehended that undesirable odor and/or excretion might leak through the waist- and leg-holes 5, 6.

For the embodiment of diaper 1 shown in FIG. 5, it is selective whether the front waist region 20 is placed upon the crotch region 21 or the rear waist region 22 is placed upon the crotch region 21 when the used diaper 1 is folded in two. In the latter case, the free end zone 7a of the auxiliary sheet 7 lying in the front waist region 20 is pulled toward the crotch region 21, then the auxiliary sheet 7 is folded back toward the front waist region 20 and the used diaper 1 is tucked away in the space defined between the auxiliary sheet 7 tuned inside out and the backsheet 3.

For the embodiment of diaper 1 shown in FIG. 5, it is also possible to fix the auxiliary sheet 7 to the outer surface of the backshet 3 along a sealed zone (corresponding to the fixed end zone 7c in FIG. 1) extending parallel to the free end zone 7a across a substantially middle zone of the crotch region 21. In the diaper 1 having the auxiliary sheet 7 fixed to the backsheet 3 along the sealed zone in this manner, the auxiliary sheet 7 cooperates with the backsheet 3 to form a pair of pockets P opening toward the front and rear waist regions 20, 22 from the crotch region 21.

The topsheet 2 may be formed from a liquid-pervious sheet such as a nonwoven fabric or a porous plastic film, more preferably from a liquid-pervious and hydrophilic sheet. The backsheet 3 may be formed from a hydrophobic nonwoven fabric, a liquid-impervious plastic film or a laminated sheet consisting of a hydrophobic nonwoven fabric and a plastic film, more preferably from a breathable and liquid-impervious sheet. It is also possible to form the backsheet 3 from a composite nonwoven fabric (SMS nonwoven fabric) in which a melt blown nonwoven fabric of a high water-resistance has its both sheet surfaces sandwiched by respective sheet surfaces of two spun bond nonwoven fabric layers of high strength and flexibility.

The auxiliary sheet 7 may be formed from a nonwoven fabric, a plastic film or a laminated sheet consisting of a nonwoven fabric and a plastic film. It is also possible to use a nonwoven fabric or a plastic film both being elastically stretchable circumferentially of the diaper 1 as the auxiliary sheet 7. In this case, it is unnecessary to provide the free end zone 7a of the auxiliary sheet 7 with the elastic member 9.

The nonwoven fabric may be selected from a group including those of spun lace-, needle punch-, melt blown-, thermal bond-, spun bond- and chemical bond-types. The component fiber of the nonwoven fabric may be selected from a group including polyolefine-, polyester- and polyamide-based fibers and conjugated fiber of polyethylene/polypropylene or polyester.

The elastic member 9 may be made of elastomeric material such as a natural or synthetic rubber in the form of threads, filaments, film or ribbon.

The core comprises a mixture of fluff pulp and high absorption polymer grains compressed to a desired thickness. Fixation of the respective sheets 2, 3, 7, bonding of the core 4 and attachment of the elastic members 9, 10, 11 may be carried out using suitable adhesive such as hot melt adhesive, pressure-sensitive adhesive or a heat-sealing technique.

The fastening zone 8 may be formed not only by application of the pressure-sensitive adhesive 8b but also by attachment of a hook member so far as the backsheet 3 is formed with a nonwoven fabric. The hook member is caught in the component fibers of the nonwoven fabric and reliably functions as the fastening zone.

This invention is applicable to, in addition to the disposable diaper 1 as has been described above, other wearable articles such as training pants and incontinent pants.

The disposable wearable article of pants type according to this invention can be thrown away, after used, with the article folded merely in two. To thrown away, it is unnecessary to roll up the used article and therefore this is no anxiety that excretion discharged in the article might be squeezed out through the waist-hole and/or the leg-holes.

In the embodiment of the article in which the fixed side edge zones and the fixed end zone (sealed zone) of the auxiliary sheet are bonded to the outer surface of the backsheet, the waist-hole as well as the leg-holes of the article folded in two are completely confined within the pocket. In this way, it is not apprehended that undesirable odor and/or excretion might leak from the waist-hole as well as the leg-holes after disposal of the used article. In the embodiment of the article in which the fastening zone is formed on the outer surface of the free end zone, the opening of the pocket is sealed by means of the pressure-sensitive adhesive and thereby leakage of undesirable odor and/or excretion can be further reliably avoided.

In the embodiment of the article in which the auxiliary sheet extends from the crotch region into the front and rear waist regions, the waist-hole as well as the leg-holes of the used article folded in two can be completely confined in the space defined between the auxiliary sheet and the backsheet. Therefore, it is not apprehended that undesirable odor and/or excretion might leak through these waist- and leg-holes after disposal of the used article. For disposal of the used article according to such embodiment, the article may be folded in two to place the front waist region upon the crotch region and tucked away in the space defined between the auxiliary sheet and the backsheet with the waist- and leg-holes completely confined within this space. It is also possible to fold the used article in two so as to place the rear waist region upon the crotch region with the waist- and leg-holes completely confined within the space for disposal of the used article.

What is claimed is:

1. A pull-on disposable article comprising:

a liquid-pervious topsheet;

a liquid-pervious backsheet;

a liquid-absorbent core disposed between the liquid-pervious topsheet and the liquid-impervious backsheet;

first and second waist regions opposed to each other and connected to each other along transversely opposite site edges thereof to form a waist-hole and a pair of leg-holes;

a crotch region extending between said first and second waist regions; and an auxiliary sheet placed upon an outer surface of said liquid-impervious backsheet and extending from said crotch region into at least one of said first and second waist regions, said auxiliary sheet comprising a free end zone lying in at least one of said first and second waist regions and extending in a circumferential direction, and fixed side edge zones longitudinally extending along the transversely opposite side edges in at least one of said first and second waist regions and the crotch region, said auxiliary sheet being fixed to the outer surface of the liquid-impervious backsheet.

2. The disposable article according to claim 1, wherein said auxiliary sheet is fixed to the outer surface of said liquid-impervious backsheet along a sealed zone extending parallel to said free end zone across a substantially middle zone of said crotch region and wherein said liquid-impervious backsheet cooperates with said auxiliary sheet to form a pocket opening toward said waist-hole.

3. The disposable article according to claim 1, wherein a fastening zone adapted to fasten said auxiliary sheet to the outer surface of said backsheet extends in said circumferential direction along said free end zone of said auxiliary sheet.

4. The disposable article according to claim 1, wherein an elastically stretchable member extending in said circumferential direction is attached under tension to said free end zone.

5. The disposable article according to claim 1, wherein said auxiliary sheet is elastically stretchable in said circumferential direction and bonded under tension in said circumferential direction to the outer surface of said liquid-impervious backsheet.

6. The disposable article according to claim 1, wherein said auxiliary sheet extends from said crotch region into a front waist region of the pull-on disposable article.

* * * * *